United States Patent [19]
Gord

[11] Patent Number: 5,917,346
[45] Date of Patent: Jun. 29, 1999

[54] LOW POWER CURRENT TO FREQUENCY CONVERTER CIRCUIT FOR USE IN IMPLANTABLE SENSORS

[75] Inventor: John C. Gord, Venice, Calif.

[73] Assignee: Alfred E. Mann Foundation, Sylamr, Calif.

[21] Appl. No.: 08/928,868

[22] Filed: Sep. 12, 1997

[51] Int. Cl.[6] .............................. H03L 5/00; H03C 3/00
[52] U.S. Cl. ..................... 327/101; 327/312; 327/316; 327/323
[58] Field of Search ..................... 327/101, 312, 327/313, 315, 316, 323, 331, 332, 157, 536

[56] References Cited

U.S. PATENT DOCUMENTS

| | | | |
|---|---|---|---|
| 4,671,288 | 6/1987 | Gough | 128/635 |
| 5,497,772 | 3/1996 | Schulman, et al. | 128/635 |

*Primary Examiner*—Kenneth B. Wells
*Attorney, Agent, or Firm*—Alfred E. Mann Foundation

[57] ABSTRACT

A low power current-to-frequency converter circuit provides an output frequency signal $F_{OUT}$ having a frequency that varies as a function of a low level analog input current signal. The analog input current signal is typically generated by an implantable sensor element, designed to sense a particular substance or parameter within body tissue or fluids to which the sensor is exposed, with the magnitude of the analog signal providing a measure of the sensed substance or parameter. Conversion of the low level analog current to the output frequency signal facilitates transmission of the data signal over a shared data bus and other digital processing of the data signal. The current-to-frequency converter circuit is fabricated from low power FET-based integrated circuits, typically realized on a single integrated circuit chip, and includes an operational amplifier having its positive input terminal connected to a storage capacitor that is charged by the analog input current signal, a voltage-controlled oscillator driven by the charge (voltage) on the storage capacitor that produces the output frequency signal, and a charge pump circuit that pumps a discrete amount of charge off of the storage capacitor during each cycle of the output frequency signal.

22 Claims, 11 Drawing Sheets

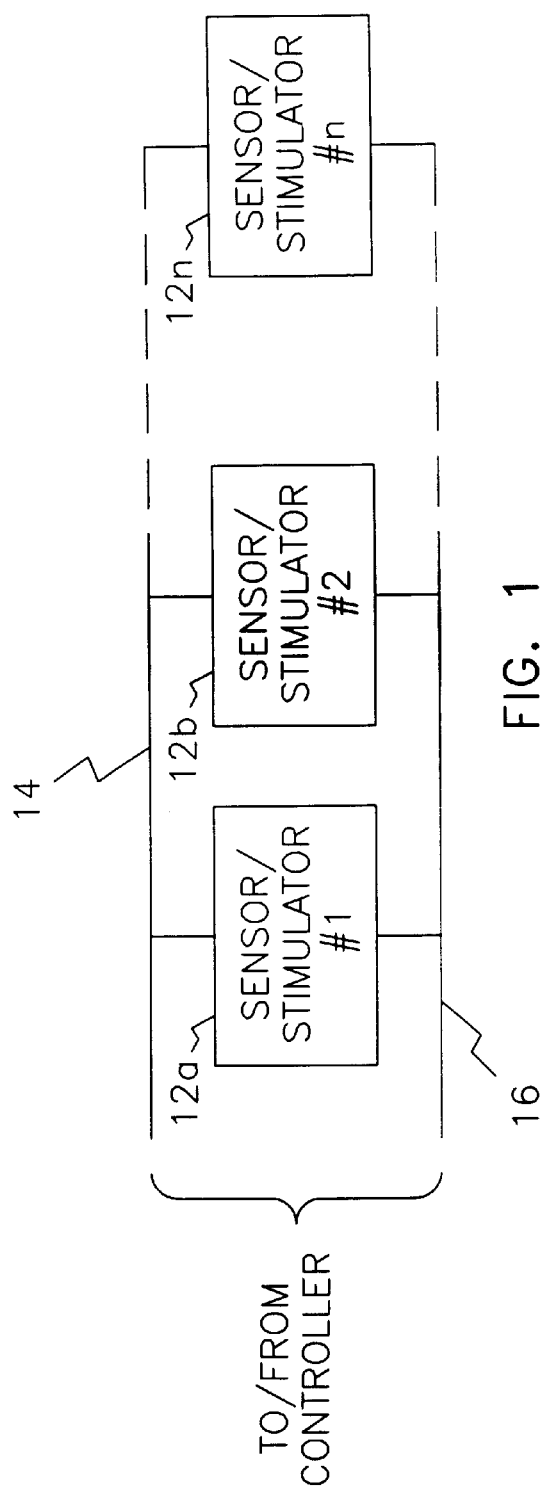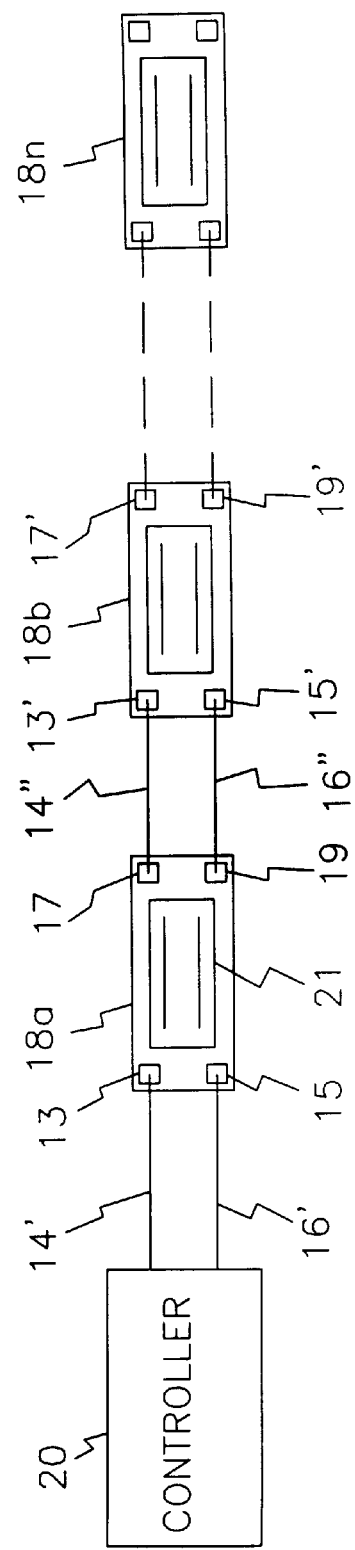

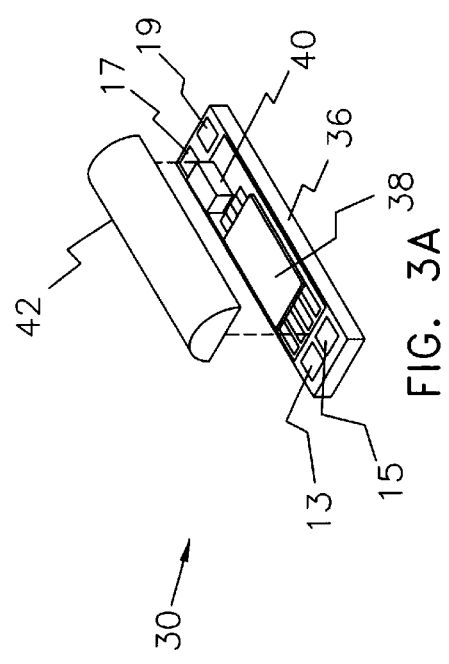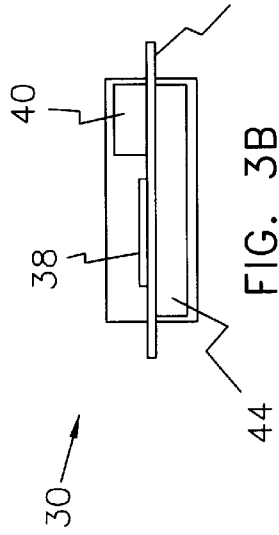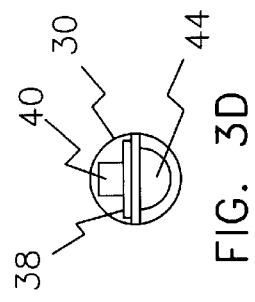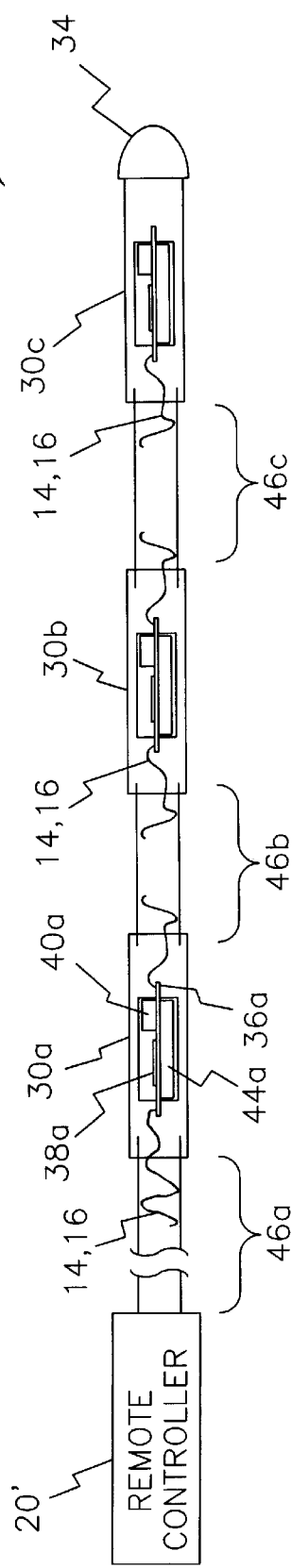

LOW POWER CURRENT TO FREQUENCY CONVERTER CIRCUIT FOR USE IN IMPLANTABLE SENSORS

FIELD OF THE INVENTION

The present invention relates to implantable medical devices, and more particularly to a very-low power current-to-frequency converter circuit that may be used within an implantable sensor to convert a small analog current, generated by the sensor as a result of having sensed a specified parameter or substance, to a variable frequency pulse train signal. A count of the pulses of the pulse train may then be made to provide an accurate digital measure of the small analog current generated from the sensor.

BACKGROUND OF THE INVENTION

In the implantable medical device field, a medical device, configured to perform a desired medical function, is implanted in the living tissue of a patient so that a desired function may be carried out as needed for the benefit of the patient. Numerous examples of implantable medical devices are known in the art, ranging from implantable pacemakers, cochlear stimulators, muscle stimulators, glucose sensors, and the like.

Some implantable medical devices are configured to perform the sensing function, i.e., to sense a particular parameter, e.g., the amount of a specified substance in the blood or tissue of the patient, and to generate an electrical signal indicative of the quantity or concentration level of the substance sensed. Such electrical signal is then coupled to a suitable controller, which may or may not be implantable, and the controller responds to the sensed information in a way to enable the medical device to perform its intended function, e.g., to display and/or record the measurement of the sensed substance. An example of an implantable medical device that performs the sensing function is shown, e.g., in U.S. Pat. No. 4,671,288.

As medical devices have become more useful and numerous in recent years, there is a continual need to provide very low power sensors that may be connected to, or incorporated within, such devices so that the desired function of the device can be carried out without the expenditure of large amounts of power (which power, for an implanted device, is usually limited.)

Moreover, as the power consumption of many implantable sensors is deliberately designed to be very low, the output signal generated by the sensor (which output signal represents a measure of the parameter or substance being sensed by the sensor) becomes very small (e.g., extremely small amplitude). This small output signal must eventually be converted to a more useful output signal, e.g., an amplified signal, or a digital signal, before it can be used to control the medical device, or be displayed by the medical device. Further, ofttimes the sensor itself is located some distance from the medical device which needs the information measured by the sensor. Hence, the sensor signal must be sent to the medical device over a suitable conductor, or otherwise transmitted to the medical device. Because the sensor output signal is so small, it generally first must be amplified, or otherwise converted to a signal in a more usable format (i.e., converted to a digital signal by an analog-to-digital (A/D) converter) before it can be reliably sent or transmitted to the medical device. Unfortunately, such amplification and/or A/D conversion requires additional circuitry, located at the sensor site. Disadvantageously, this additional circuitry located at the sensor (which may be incorporated as part of the sensor, or becomes supplemental circuitry that must be used with the sensor), not only places additional power demands on the system, but it also may dramatically increase the circuit complexity size, and cost of the sensor circuitry. What is needed, therefore, is an extremely low power conversion circuit that converts the very small output signals typically obtained from implantable sensors to a signal format that facilitates the signal's subsequent transmission to and use by the medical device.

The above need is even more acute where more than one sensor must be used. More than one sensor may be needed, for example, to measure more than one substance or physiological parameter. In other instances, more than one sensor may be needed to measure or sense the same substance or physiological parameter at different locations within the patient's body. Whenever multiple sensors are implanted and are intended to be used in concert to achieve a desired medical function, there is a corresponding need to connect or couple such separate multiple sensors to a single control circuit or common control point. Hence, there is a critical need that the output signal (representing output data) from each sensor be first converted to a format that facilitates transmission of the sensor output signal over a shared data bus or communication channel without compromising the integrity of the data, and that such conversion not consume large or even moderate, amounts of power.

SUMMARY OF THE INVENTION

The present invention addresses the above and other needs by providing a very low power current-to-frequency (I-to-F) converter circuit for use on-site with an implantable sensor that generates a low level analog current or voltage as its output signal.

In accordance with one aspect of the invention, the analog output signal generated by the sensor comprises a very small analog electrical current, e.g., having a peak magnitude on the order of only about 100 nanoamps, and the converter circuit utilized by the implantable device comprises a low power current-to-frequency converter circuit. Such low power current-to-frequency converter circuit includes: (1) an operational amplifier, (2) a first capacitor, (3) a voltage controlled oscillator (VCO), and (4) a charge pump circuit.

The operational amplifier, preferably fabricated from low power N-MOS and P-MOS FET transistors having specific dimensions, has two input terminals and one output terminal In operation, it differentially amplifies an electrical signal applied between its two input terminals to provide an amplified output signal appearing on its output terminal. The first capacitor is connected to one of the input terminals of the operational amplifier, and is used to receive the charge provided by the input electrical current. The VCO circuit has a voltage-control input terminal and a VCO output terminal, and the voltage-control input terminal is connected to the output terminal of the operational amplifier. The VCO, as is known in the art, includes means for generating a VCO signal having a frequency that varies as a function of the magnitude of a control voltage applied to the voltage-control input.

In operation, the charge-pump circuit is coupled to the first capacitor of the operational amplifier and pumps a discrete charge off of the first capacitor under control of the frequency of the VCO signal. An electrical current applied to the first capacitor, e.g., from the output of the sensor, tends to cause a charge to accumulate on the first capacitor as a function of the magnitude of the electrical current, which charge tends to increase the output voltage of the operational amplifier so as to increase the frequency of the VCO signal. This increased VCO frequency, in turn, causes the charge to be pumped off of the first capacitor at an increased rate. The operational amplifier thereby forces the frequency of the VCO signal to whatever rate is needed to maintain the charge on the first capacitor at essentially zero. In this manner, the frequency of the VCO signal varies as a function of the magnitude of the electrical current applied to the first capacitor.

Advantageously, in a preferred embodiment, the operational amplifier, VCO and charge pump circuit all operate using just one supply voltage having a first terminal V+, and a second terminal V- (which two terminals may sometimes be referred to as simply V and "ground"). The first capacitor is connected between a first input terminal of the operational amplifier and V-, and a second input terminal of the operational amplifier is also connected to V-. Using one supply voltage in this manner keeps the power consumption of the current-to-frequency converter very low. For example, in a preferred design, the low power current-to-frequency converter circuit consumes less than about 600 nanoamps (na) of current.

In accordance with yet another aspect of the invention, the I-to-F converter circuit may be included within the hermetically-sealed part of an implantable sensor that includes both a non-hermetically sealed part (containing, e.g., electrodes, connection terminals, and/or sensor materials that must be in contact with body fluids or tissue) and an hermetically sealed part (containing electrical circuitry to manage, monitor and/or control the non-hermetically sealed part). A first pair of terminals is included as part of the non-hermetically sealed part and functions as the input/output terminals for connecting the implantable sensor to an implantable medical device over a connection bus that includes just two conductors, one conductor being connected to each terminal. Both operating power and control data are transmitted over the two-conductor bus from the medical device to the sensor; and sensed data, converted to a suitable form for transmission by the I-to-F converter of the present invention, is transmitted over the same two-conductor bus from the implantable sensor to the medical device. The first pair terminals (or a second pair of terminals electrically connected to the first pair of terminals), may also function as connection terminals for attaching additional implantable sensors to the connection bus, in daisy-chain fashion, as disclosed in applicant's copending patent, entitled DAISY-CHAINABLE SENSORS AND STIMULATORS FOR IMPLANTATION IN LIVING TISSUE, Ser. No. 08/928,867, filed Sep. 12, 1997 (Attorney Docket No. 56287).

Yet a further aspect of the invention is that the I-to-F converter circuit may be realized on a single integrated circuit chip.

It is thus a feature of the present invention to provide a very low power, implantable, current-to-frequency conversion circuit for use within an implantable sensor, e.g., an implantable glucose sensor, that generates a small analog electrical current as a function of a sensed physiological parameter or substance.

It is another feature of the invention to provide a very low power, implantable I-to-F converter circuit that accumulates input current (I) on a storage capacitor, generates a control voltage as a function of the charge on the storage capacitor, drives a VCO with the control voltage so as to produce a VCO output signal having a frequency (F) that varies as a function of the control voltage, and pumps a discrete charge off of the first capacitor under control of the frequency of the VCO signal so as to maintain the charge on the first capacitor at approximately zero, thereby converting input current (I) to an output frequency (F).

It is yet another feature of the invention to provide an implantable sensor having an hermetically sealed part and a non-hermetically sealed part, with electrical feed-through means for making electrical connections between the hermetically sealed part and the non-hermetically sealed part, and with a low power I-to-F converter circuit being included in the hermetically-sealed part.

BRIEF DESCRIPTION OF THE DRAWINGS

The above and other aspects, features and advantages of the present invention will be more apparent from the following more particular description thereof, presented in conjunction with the following drawings wherein:

FIG. 1 is a block diagram that illustrates multiple sensors/stimulators connected together using a two-conductor bus, which two-conductor bus may be connected to a controller;

FIG. 2 schematically illustrates a preferred manner of how a sensor made in accordance with the present invention may be connected with a controller and other sensors in a serial or daisy-chain fashion;

FIG. 3A shows a perspective, partially exploded, view of a sensor of the type used in the daisy chain of FIG. 2;

FIG. 3B illustrates a sectional side view of the sensor of FIG. 3A;

FIG. 3C illustrates a sectional top view of the sensor of FIG. 3A;

FIG. 3D illustrates a sectional end view of the sensor of FIG. 3A;

FIG. 4 depicts an implantable lead that includes a plurality of the sensors of FIGS. 3A–3D;

Figure 5A:
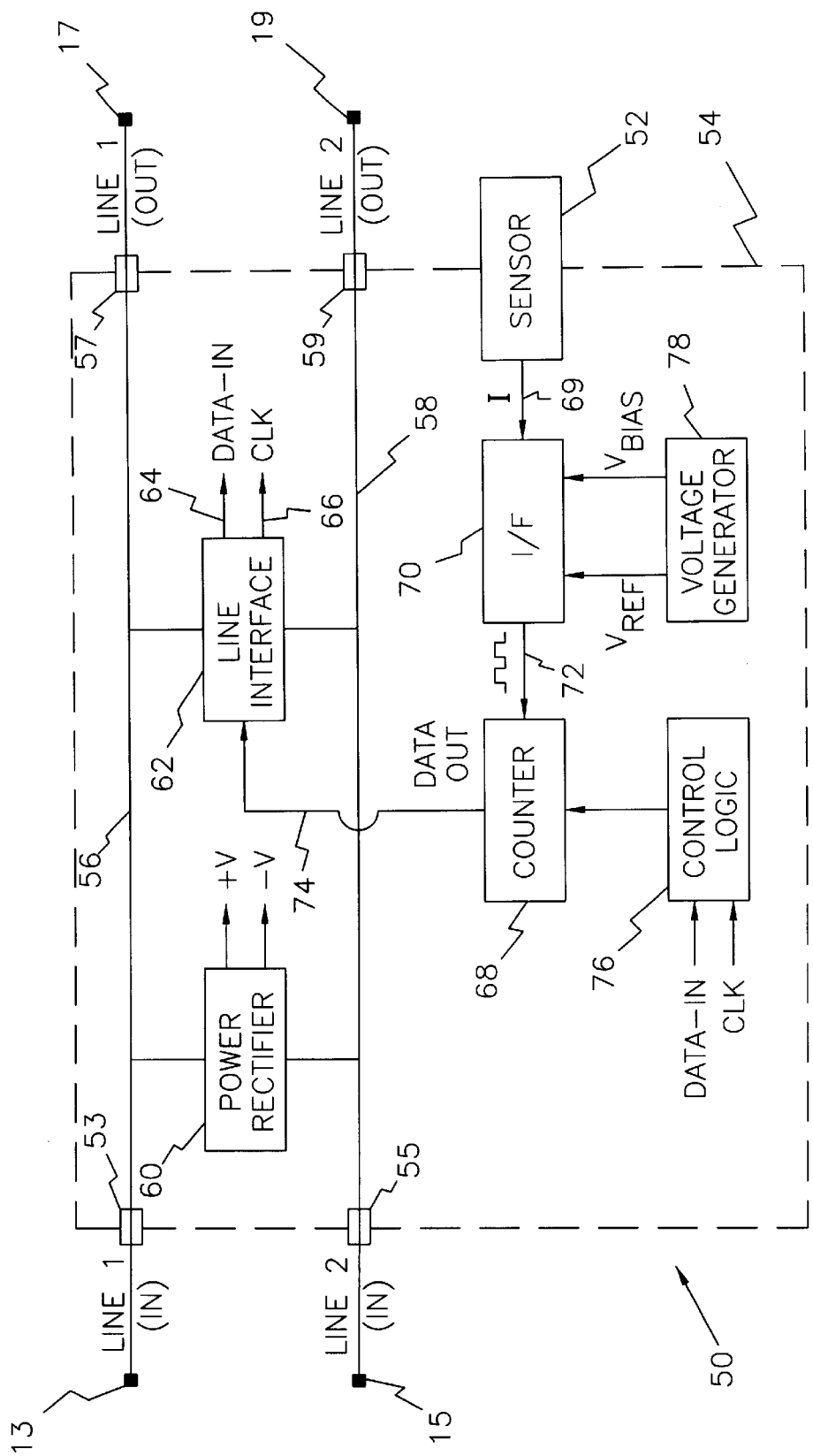
FIG. 5A is a functional block diagram of a simple daisy-chainable implantable sensor that includes an I-to-F converter circuit in accordance with the present invention.
Figure 5B:
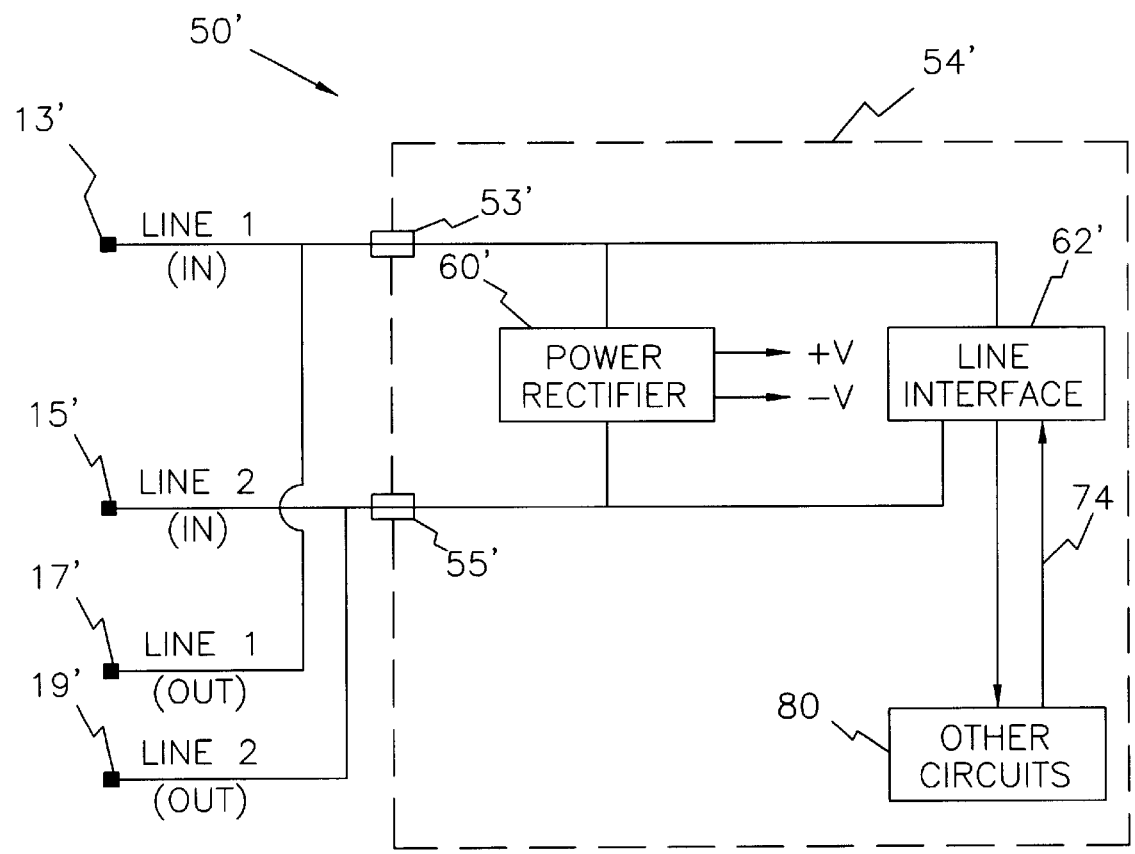
FIG. 5B is a functional block diagram as in FIG. 5A, but wherein an alternate connection scheme is used for attaching additional sensors.
Figure 5C:
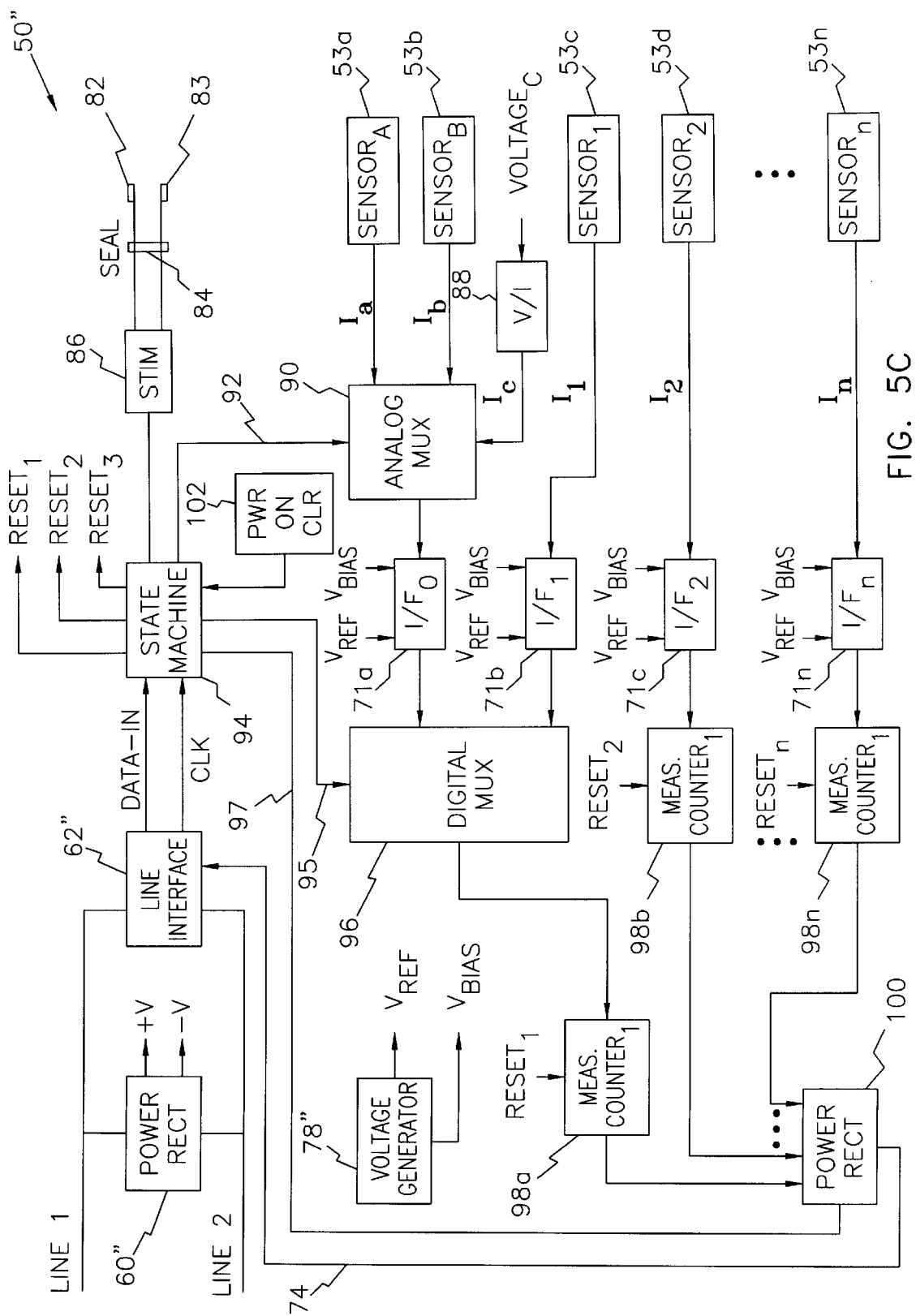
FIG. 5C is a functional block diagram as in FIG. 5A but wherein additional circuit functions are provided so that a wide variety of different sensors and a stimulator may be included within the same implantable sensor device, and wherein multiple I-to-F converter circuits are included as part of the device.

Corresponding reference characters indicate corresponding components throughout the several views of the drawings; and a generic reference to "FIG. 3", "FIG. 5" or "FIG. 10" refers respectively to all of the figures associated with that number, i.e., a generic reference to "FIG. 3" refers to all of FIGS. 3A, 3B, 3C and 3D; a generic reference to "FIG. 5" refers to all of FIGS. 5A, 5B and 5C; and a generic reference to "FIG. 10" refers to FIGS. 10A, 10B, 10C and 10D.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention relates to a very low power current-to-frequency (I-to-F) converter circuit, described more fully below in connection with FIGS. 9–10. It is the purpose of the I-to-F converter circuit to convert an analog input signal, i.e., a very low amplitude electrical current, to a variable frequency output signal Such output signal has a frequency that varies as a function of the magnitude of the analog input current.

The I-to-F converter circuit provided by the present invention is especially well suited for use within an implantable sensor of the type described in connection with FIGS. 1–8. It is to be understood, however, that the invention is not limited to use only within sensors of the type described in connection with in FIGS. 1–8; rather the sensors and sensor systems of the type described in connection with FIGS. 1–8 merely represent the best mode currently contemplated for using an I-to-F converter circuit within an implantable sensor. Because a thorough understanding of such sensors should not be necessary to appreciate and understand the salient features of the I-to-F converter circuit described herein, but because a general understanding of such sensors may help provide useful background information to one way the invention may be used, only a cursory explanation of FIGS. 1–8 will be provided herein. A more thorough description of each of FIGS. 1–8 may be found in applicant's copending patent application entitled : DAISY-CHAINABLE SENSORS AND STIMULATORS FOR IMPLANTATION IN LIVING TISSUE, Ser. No. 08/928,867, filed Sep. 12, 1997 (Attorney Docket No. 56287).

Turning then, first to FIG. 1, there is shown a block diagram that illustrates multiple sensors $12a$, $12b$, . . . $12n$, or other implantable devices, connected together, as well as a controller (not shown in FIG. 1) using just two common conductors 14 and 16. The two conductors 14 and 16, commonly referred to as a two-conductor connection "bus", provide a common signal and return for data signals and power signals that are sent from the controller to the devices $12a$, $12b$, . . . $12n$, as well as a common signal and return path for data signals transmitted from the devices $12a$, $12b$, . . . $12n$, to the controller.

FIG. 2 schematically illustrates how an implantable sensor/stimulator $18a$ be connected with a remote controller 20 and other implantable devices $18b$, . . . $18n$, in a serial or daisy-chain fashion. As seen in FIG. 2, the device $18a$ is connected to the controller 20 by two conductors 14' and 16' of the connection bus, which are attached to a first pair of pads or terminals 13 and 15 along a proximal side (i.e., the side closest to the controller 20) of the device $18a$. Another pair of pads or terminals 17 and 19 are located along a distal side (i.e., the side farthest from the controller 20) of the device $18a$. The distal pad 17 is electrically connected to the proximal pad 13 through the circuitry 21 located on the device $18a$. Similarly, the distal pad 19 is electrically connected to the proximal pad 15 through the circuitry 21 included within the device $18a$. Two additional conductors 14" and 16" are then used to connect the distal pads 17 and 19 of the device $18a$ to corresponding proximal pads 13' and 15' of the next device $18b$ connected in the daisy chain. In this manner, as many devices as desired may be serially connected to the controlled 20 using just two conductors.

There exist many different applications for the daisy-chainable sensors 12 or 18 illustrated in FIGS. 1 or 2. Generally, where the sensor 12 or 18 is implanted, it is designed to sense one or more body parameters or substances found in body tissue or fluids, e.g., glucose level, blood pH, $O_2$, temperature, or the like. Such measurements can provide valuable information regarding the condition and status of the patient.

Turning next to FIGS. 3A, 3B, 3C and 3D, there are shown, respectively, a perspective exploded view (FIG. 3A), a side view (FIG. 3B), a top view (FIG. 3C), and an end view (FIG. 3D), of a typical implantable sensor device 30 of a type suited for use with the present invention. As seen best in FIG. 3A, the sensor device 30 typically includes a carrier or substrate 36 on which an integrated circuit (IC) 38 and other components, such as a capacitor 40, are mounted. In some embodiments, it should be noted that the carrier or substrate 36 may actually comprise the substrate on which the IC 38 is fabricated; but for purposes of the explanation which follows, it is assumed that a separate substrate or carrier 36 is employed with various circuit elements mounted thereon to form a hybrid circuit. The carrier or substrate has conductive patterns etched or otherwise deposited thereon to interconnect the IC 38, capacitor 40, and any other components to form a hybrid circuit which carries out the desired sensing (or other) function.

All of the components of the hybrid circuit are hermetically sealed within a cavity formed by a lid or cover 42 which is bonded to the substrate 36. Proximal pads or terminals 13 and 15, as well as distal pads or terminals 17 and 19, remain outside of the hermetically sealed part of the hybrid circuit. These proximal and distal pads, however, are electrically connected to the circuitry within the hermetically sealed part through suitable feedthrough connections. One manner of making such feedthrough connection is to use a feedthru connection that passes through the carrier or substrate in the stair-step manner (including both vertical and horizontal segments) disclosed in U.S. Pat. No. 5,750,926 entitled "Hermetically-Sealed Electrical Feedthrough For Use With Implantable Electronic Devices", which patent is assigned to the same assignee as is the instant application, and which patent is incorporated herein by reference.

On the side of the carrier or substrate opposite the hybrid electrical circuitry a suitable electrochemical sensor 44, or other desired type of sensor or stimulator, may be formed or located. A type of electrochemical sensor that may be used, for example, is the enzyme electrode sensor described in U.S. Pat. No. 5,497,772, incorporated herein by reference, and in particular, in FIGS. 2A, 23, 2C, 3, 4A and 4B of that patent.

For purposes of the present invention, the precise nature of the sensor 44, or other implantable element used within the device 30, is not critical. All that matters is that the sensor or other element be implantable, and that it provide a desired function, e.g., sense a certain type of parameter of substance, or generate a certain type of signal, in response to an appropriate control signal or signals.

Signal communication between the hybrid circuit side of the substrate or carrier 36 (which is the top side as the device 30 is oriented in FIG. 3B or FIG. 3D, and which top side includes the hermetically sealed portion of the device) and the sensor side of the device 30 (which is the bottom side as shown in FIG. 3B or 3D) is achieved by way of appropriate hermetically-sealed feedthroughs that pass step-wise from the hybrid (top) side of the device 30 through the substrate or carrier, e.g., in the manner set forth in the above-referenced patent application '559.

The configuration illustrated in FIG. 2 is especially well-suited where several of the implantable devices are to be daisy-chained together to form a single lead 32, as shown in FIG. 4. As seen in FIG. 4, three sensor-type devices 30a, 30b, and 30c are connected together via lead segments 46a, 46b, and 46c. Each of the lead segments 46a, 46b, and 46c, contain two conductors 14, 16, and may be constructed in any suitable manner, e.g., with the two conductors being spirally wound within the lead segments, and with the spiral windings being encased or covered within a sheath of silicone rubber, as is known in the lead art. A distal cap 34 covers the distal pads of the end, or most-distal, device 30c of the lead 32.

The low power current-to-frequency converter circuit of the present invention may be included as part of the electrical circuitry contained within or included as a part of what is referred to above as the "hybrid circuit portion" of the implantable device 30. In general, such electrical circuitry allows the implantable device 30 to be daisy chained with other similar implantable devices, while still allowing each individual device to be individually addressed, controlled and monitored from a single controller 20. In particular, the I-to-F converter circuit of the present invention converts low level analog signals obtained from the sensor 44, or elsewhere, to be converted to a frequency, which frequency can then be easily counted over a fixed time period to create a digital signal representative of the sensor's analog output. Such digital signal can thereafter be more reliably transmitted over the two-conductor bus to the controller 20.

The circuitry included within the hermetically-sealed portion of the device 30 may take many and varied forms. FIGS. 5A, 5B and 5C show three such variations. FIG. 5A, for example, is a functional block diagram of a basic configuration of control/interface circuitry 50 for use with a sensor 52. The dotted line 54 represents an hermetic seal that hermetically seals the circuitry 50 and all but a portion of the sensor 52. The input pads 13 and 15, as well as the output pads 17 and 19, are not hermetically sealed, thereby allowing these pads to be readily connected to the two conductors 14 and 16 (FIG. 1) from the controller 20.

As seen in FIG. 5A, pads 13 and 15 are connected to respective conductive traces, labeled LINE 1 (IN) and LINE 2 (IN) representing the two conductors of the two-conductor bus that connects the device 30 to its controller 20, or to other devices. Each of the LINE 1 and LINE 2 conductive traces passes through respective feedthroughs 53 and 55 into the hermetically sealed portion of the circuitry 50. Pads 17 and 19, on the other side of the circuit, are likewise connected to respective conductive traces, labeled LINE 1 (OUT) and LINE 2 (OUT), and each of these conductive traces passes through respective feedthroughs 57 and 59 into the hermetically sealed portion 54 of the circuitry 50. Inside the hermetically sealed portion, LINE 1 (IN) connects with LINE 1 (OUT) via conductive trace 56, and LINE 2 (IN) connects with LINE 2 (OUT) via conductive trace 58. In this manner, pad 13 is electrically connected with pad 17 via trace 56 which passes through the hermetically sealed portion 54 between feedthroughs 53 and 57. This interconnection of pad 13, trace 56 and pad 57 is referred to hereafter simply as LINE 1. Similarly, pad 15 is electrically connected with pad 19 via trace 58, which trace also passes through the hermetically sealed portion 54 between feedthroughs 55 and 59. This interconnection is referred to hereafter as LINE 2.

As seen in FIG. 5A, a power rectifier circuit 60 is connected between LINE 1 and LINE 2. This circuit extracts and rectifies any signal pulses found on LINE 1 and LINE 2 and produces an operating voltage, +V and −V, for powering the circuitry 50. Such rectification is not a trivial task given the low level signals which are generally present on LINE 1 and LINE 2. Details of such circuitry may be found in applicant's copending patent application A LOW POWER RECTIFIER CIRCUIT FOR IMPLANTABLE DEVICES, Ser. No. 08/928,871; filed Sep. 12, 1997 (Attorney Docket No. 57795), incorporated herein by reference.

A line interface circuit 62 also is connected between LINE 1 and LINE 2. The circuit 62 functions as an interface between the circuitry 50 and LINE 1 and LINE 2. To this end, the interface circuit 50 receives incoming data pulses present on LINE 1/LINE 2 and generates a DATA-IN signal on line 64 therefrom The interface circuit 62 further generates a clock (CLK) signal on line 66 that is synchronized with the incoming data signals The interface circuit 50 also receives digital output data, DATA OUT, from a counter circuit 68, and converts this output data to an appropriate format prior to placing the output data back on LINE 1/LINE 2. One type of line interface circuit 62 that may be used with the circuitry 50 is illustrated in the schematic diagram shown and explained below in conjunction with FIG. 9.

Still referring to FIG. 5A, the sensor 52 may be any suitable sensor adapted to sense a desired condition, parameter, or substance present (or absent) in the implantable tissue within which the device 30 is implanted. For example, the sensor 52 may comprise a glucose sensor that generates an output analog current, I, appearing on line 69, having a magnitude that varies as a function of the sensed glucose.

As a practical matter, regardless of the type of sensor 52 that is employed, it will usually generate either an analog output voltage or an analog output current as a function of the concentration, magnitude, composition, or other attribute, of the parameter being sensed. Such analog current or voltage may then be converted, using an appropriate converter circuit 70, to a frequency signal, appearing on line 72. Typically, the frequency signal on line 72 comprises a train of pulses having a frequency (or repetition rate) that varies as a function of the input voltage or current. In FIG. 5A, for example, it is assumed that the sensor 52 generates an output current I, and that the converter circuit 70 comprises a current-to-frequency (I-to-F) converter circuit, generating an output pulse train on line 72 that has a frequency which varies as the magnitude of the current I varies. It is this I-to-F converter circuit 70, or an equivalent converter circuit, that comprises the subject matter of the present invention.

Once a pulse train 72, or other ac signal, is generated having a frequency which varies as a function of the parameter being sensed by the sensor 52, such signal is applied to a counter circuit 68. (Note, as a shorthand notation used in this application, a signal appearing on signal line having a given reference number may be referred to as the signal having such given reference number, i.e., the signal appearing on signal line 72 may simply be referred to as "signal 72".) The counter circuit simply counts the number of pulses present in the signal 72 over a prescribed period of time, e.g., a fixed time window of 1 second, thereby providing a measure of the frequency of the signal 72. In this manner, by resetting the counter 68 at the beginning of each measurement period, the count held in the counter at the end of the measurement period provides a signal representative of the frequency of the signal 72. Such count signal, for the basic embodiment shown in FIG. 5A, may thus serve as the output data signal, DATA OUT, that is sent to the line interface circuit 62 over signal line 74.

Control of the counter 68, i.e., resetting the counter and/or stopping the counter after a prescribed measurement period, is controlled by control logic 76. In a simple embodiment, the measurement period may be a fixed time period In other embodiments, the measurement period may be set by input data received over signal line 64 from the line interface circuit 62. The clock signal 66 may be used as a measure of elapsed time, as well as to coordinate when the counter 68 sends its DATA OUT signal 74 to the line interface circuit 62.

As needed, a voltage generator circuit 78 generates a reference voltage $V_{REF}$, and one or more bias signal(s), $V_{BIAS}$, that are used by the current-to-frequency (I-to-F) converter circuit 70 as it performs its function of converting the analog current signal 69 to a frequency signal 72, as explained more fully below in connection with FIGS. 9 and 10.

In a similar manner, one or more I-to-F converter circuits may be used within the devices illustrated in FIGS. 5B and 5C, as described in the above-referenced copending patent application, entitled: DAISY-CHAINABLE SENSORS AND STIMULATORS FOR IMPLANTATION IN LIVING TISSUE.

Figure 6:
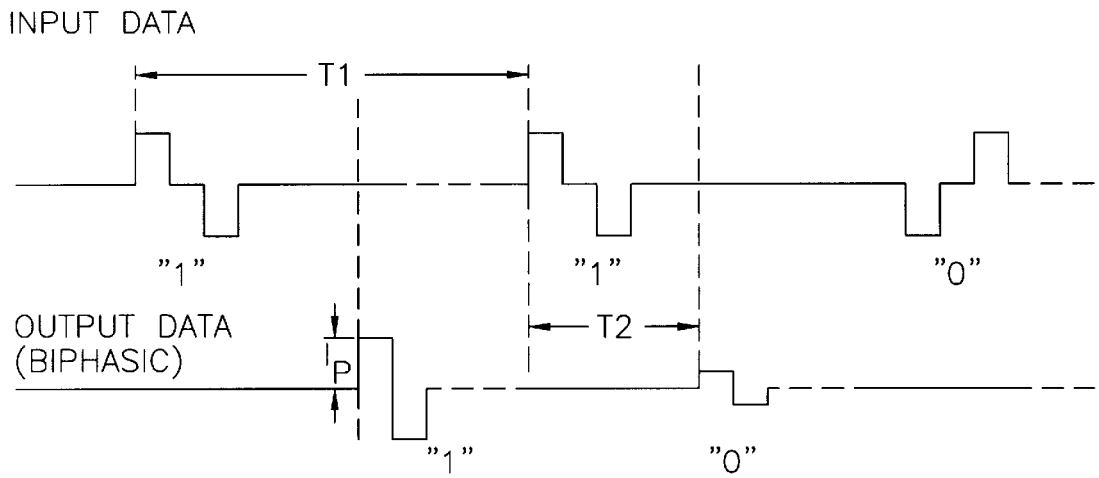
FIG. 6 is a timing diagram that illustrates input and output data sent to and received from an implantable sensor of the type shown in FIG. 5A, 5B or 5C.

Turning back momentarily to FIG. 2, where a plurality of implantable, daisy-chainable sensors 18a, 18b . . . 18n are shown connected in tandem, a preferred manner of operation is for the controller 20 to provide operating power to, as well as to individually address and send data to and receive data from, each of the devices 18 that are connected thereto over the two-conductor bus made up of the conductors 14 and 16. One manner in which such powering and individual addressing is done is as shown in connection with FIGS. 6, 7 and 8. FIG. 6 illustrates, for example, a timing diagram that shows a preferred relationship between input data (top waveform) sent to the implantable devices and output data (bottom waveform) received from the implantable devices, as such data appears on the two LINE 1/LINE 2 conductors that connect all of the devices together. As seen in FIG. 6, the preferred form for the input data is biphasic pulses. Each biphasic pulses comprises a first current pulse of a first polarity, followed by a second current pulse of the same magnitude of the opposite polarity. Thus, the net current for each biphasic pulse is preferably zero, with the positive current pulse effectively balancing out the negative current pulse. The typical widths of the current pulses are from 1 to 100 microseconds ($\mu$sec), with the magnitude of each current pulse typically ranging from 10 to 1000 microamps. A binary or logical "1" is represented by a biphasic pulse of one phase, e.g., a positive current pulse followed by a negative current pulse; while a binary or logical "0" is represented by a biphasic pulse of the opposite phase, e.g., a negative pulse followed by a positive pulse. Thus, as shown in FIG. 6, a binary "1" may be represented as a positive current pulse followed by a negative current pulse, while a binary "0" is represented by a negative current pulse followed by a positive current pulse.

As also seen in FIG. 6, the preferred form for the output data is also a biphasic pulse, amplitude modulated (or preferably ON/OFF modulated) as a function of whether the output data is a binary "1" or "0". In a preferred embodiment, the peak amplitude of the output data pulse for a binary "1" is $I_P$, while the peak amplitude of the output data pulse for a binary "0" is zero. Thus, in this preferred ON/OFF modulation scheme, the presence of an output data pulse represents a binary "1" and the absence of an output data pulse represents a binary "0". Output data pulses are inserted in the data stream appearing on the LINE 1/LINE 2 conductors pulses at a specified time T2 from the input data pulse so as to fall between the input data pulses, in a time-division multiplexed manner. Although the preferred form of the output data pulses is a biphasic pulse (to achieve current balancing), it is noted that in some instances a monophasic pulse at time T2 (and with amplitude of $I_P$ or zero) may be used.

Figure 7:
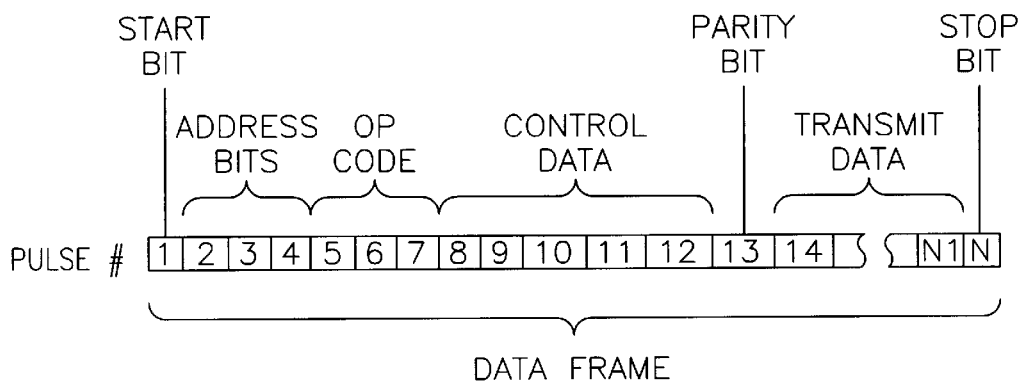
FIG. 7 illustrates a data frame used to communicate with the implantable sensor of the present invention.
Figure 8:
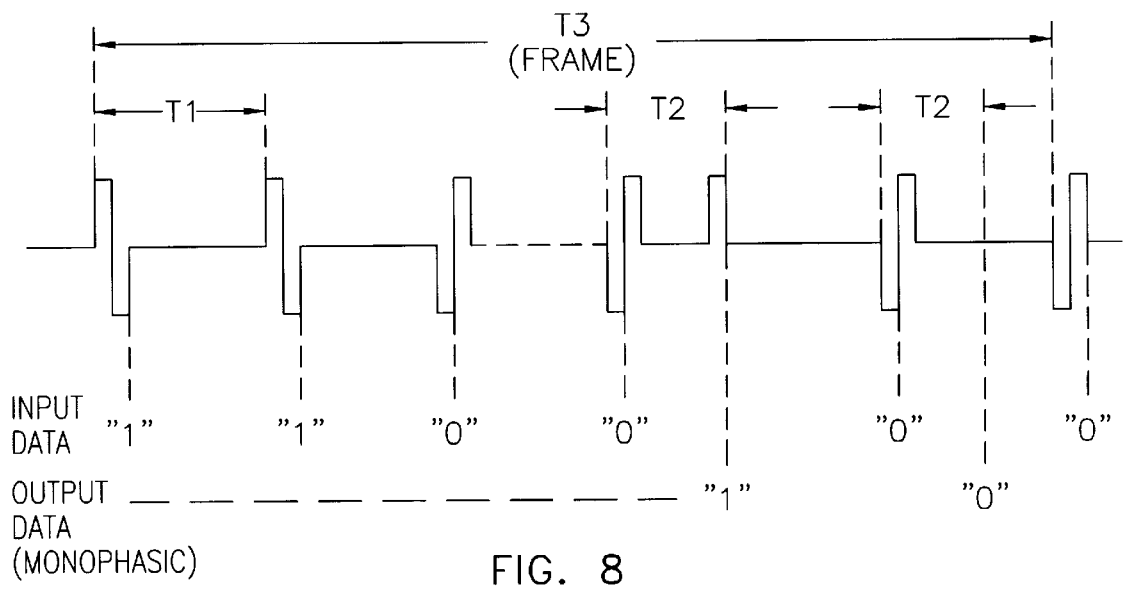
FIG. 8 is a timing diagram that illustrates time multiplexed input and output data within a data frame as it appears on the two-conductor bus connecting a plurality of daisy-chainable devices of the type shown in FIG. 5A, 5B or 5C.

As shown in FIGS. 7 and 8, the input data sent over the LINE 1/LINE 2 conductors by the controller is divided into data frames of length T3. Within each data frame, N bits of data are found, where N is an integer typically ranging from 8 to 64. A representative assignment of the data bits included in the data frame is illustrated in FIG. 7.

Because the input data comprises biphasic pulses that occur at a regular interval or rate (e.g., every T1 seconds), the energy contained in such pulses may be utilized to provide the operating power for the circuits contained within the device 50". Such is accomplished using the rectifier circuit 60, 60' or 60" (FIGS. 5A, 5B or 5C).

The input and output data pulses of the type shown in FIGS. 6 and 8 are generated by the line interface circuit 62, 62' or 62" (FIGS. 5A, 5B or 5C). A schematic diagram of a preferred line interface circuit is described in the above-referenced copending patent application, DAISY-CHAINABLE SENSORS AND STIMULATORS FOR IMPLANTATION IN LIVING TISSUE, Ser. No. 08/928, 867, filed Sep. 12, 1997 (Attorney Docket No. 56287). See particularly FIG. 9 of the referenced application, and its accompanying text.

Figure 9:
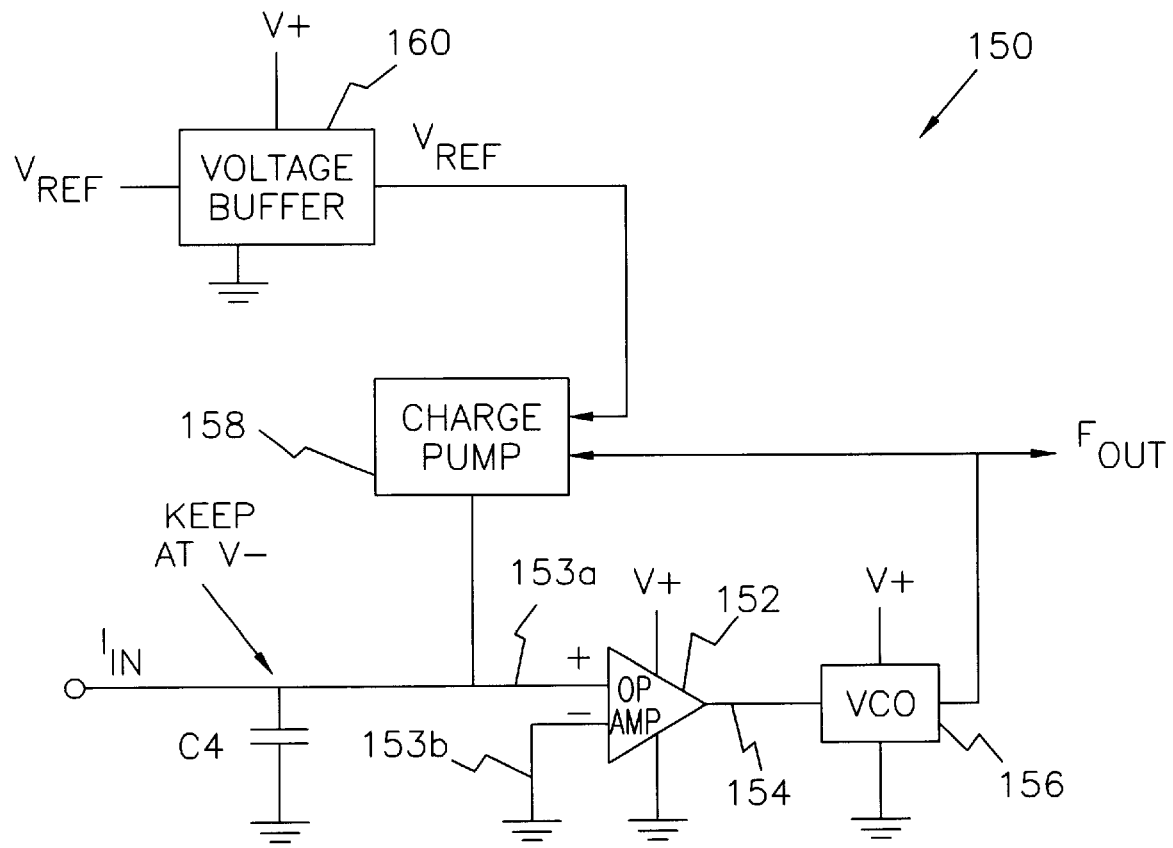
FIG. 9 shows a functional block diagram of a I-to-F converter circuit made in accordance with the present invention.

With reference next to FIG. 9, there is shown a block diagram of a low power current-to-frequency converter circuit 150 made in accordance with the present invention. As seen in FIG. 9, the current-to-frequency converter 150 includes four main functional elements These four main functional elements include: (1) an operational amplifier 152 having a positive input terminal 153a and a negative input terminal 153b, and an output terminal 154; (2) a capacitor C4 connected to the positive input terminal 153a of the operational amplifier 152; (3) a voltage controlled oscillator (VCO) circuit 156 having a voltage-control input terminal and a VCO output terminal, the VCO input terminal being connected to the output terminal 154 of the operational amplifier 154, and the VCO output terminal providing a variable frequency output signal $F_{OUT}$; and (4) a charge-pump circuit 158 coupled to capacitor C4 (i.e., also connected to positive input terminal 153a of the operational amplifier 152.

In operations the analog input signal, $I_{IN}$, charges up the capacitor C4. The amount of charge accumulated by capacitor C4 is a function of the magnitude of the input current $I_{IN}$, which input current reflects a measure of the parameter or other condition being sensed by the sensor or otherwise monitored from within the implantable device 30. The charge pump circuit 158 pumps a discrete charge (i.e., a fixed number of coulombs) off of capacitor C4 during each cycle of the $F_{OUT}$ signal generated by the VCO 156. The operational amplifier 152 differentially amplifies an electrical signal applied between its two input terminals 153a and 153b to produce an amplified output signal on its output terminal 154. Because the negative input terminal 153b is grounded, the differential input signal applied to the operational amplifier 152 is effectively the amount of charge, or voltage, that has accumulated on the capacitor C4. Thus, the amplified output signal from the operational amplifier 152 comprises a voltage that varies as a function of the input current $I_{IN}$. This amplified output signal is applied to the VCO 156 as a control voltage, causing the frequency output signal, $F_{OUT}$, of the VCO to have a frequency that varies as a function of the input current, $I_{IN}$.

The output frequency signal from the VCO, $F_{OUT}$, besides being available as a variable frequency output signal $F_{OUT}$ that can be counted over a fixed period of time (as described above in connection with FIG. 5A), is also applied to the charge pump circuit 158. This output frequency signal $F_{OUT}$ typically comprises a pulse train, the frequency of which varies as a function of the magnitude of a voltage applied to the voltage-control input. For each pulse of the variable frequency pulse train $F_{OUT}$, the charge pump circuit 158 pumps a discrete charge off of the capacitor C4. Thus, it is seen that the input current $I_{IN}$ causes a charge to accumulate on capacitor C4, which charge tends to increase the output voltage of the operational amplifier 152 so as to increase the frequency of the $F_{OUT}$ output signal. This increased frequency, in turn, causes the charge that is pumped off of the capacitor C4 to increase (or to occur at an increased rate). The net result is that the operational amplifier 152, by amplifying the charge accumulated on capacitor C4 in this manner, forces the frequency of the $F_{OUT}$ signal to whatever rate is needed to maintain the net charge on the capacitor C4 at essentially zero. As a result, the frequency of the $F_{OUT}$ signal varies as a function of the magnitude of the electrical current $I_{IN}$ applied to the capacitor C4, and the desired current-to-frequency (I-to-F) conversion is thus achieved.

As needed, and as explained more fully below in connection with FIG. 10, a voltage buffer circuit 160 may be employed as part of the I-to-F conversion circuit 150 of FIG. 9 to produce a stable and isolated reference voltage $V_{REF}$, which reference voltage is used by the charge pump circuit 158 as it performs its charge pumping function.

While less elaborate I-to-F converter circuits than the circuit 150 of FIG. 9 could and have been devised by those of skill in the art, the advantageous feature of the I-to-F circuit 150 of FIG. 9 is that it can be configured, using low power FET transistors, to operate so as to consume very little power. Such a low power configuration is shown and described below in connection with FIGS. 10A, 10B, 10C and 10D.

Turning next, then, to FIGS. 10A, 10B, 10C, and 10D, schematic and/or logic diagrams of a preferred low power I-to-F converter circuit made in accordance with the best mode presently contemplated for practicing the invention is illustrated. The I-to-F converter circuit 150 is preferably realized using a miniature integrated circuit (IC), configured, e.g., with specific combinations of N-channel and P-channel field effect transistors (FETs), denoted as "N-FET" and "P-FET" transistors, formed on a common substrate, and specifically designed for low power consumption. The preferred sizes (length and width) of each of the relevant N-FET or P-FET transistors are listed in Table 1, along with other component values of interest. The N-FET and P-FET dimensions shown in Table 1 relate to the relative size of each transistor as it is formed on the IC substrate. More particularly, an N-FET, for example, having a size of "5/10" means that the width of the source to drain channel is 5 microns (where "micron" means one micrometer, also written as 1 $\mu$m, or $1\times10^{-6}$ meters), and the length of the channel is 10 microns. This type of characterization (by dimension or size) of the various N-FET and P-FET transistors used within an IC is known and understood by those of skill in the semiconductor processing art. Advantageously, by selectively controlling the size (dimensions) of such transistors during the IC processing steps, the performance of the FET transistors can be controlled or tailored for the specific design for which the transistor is used. Thus a relatively "long" N-FET, having a size of, e.g., 5/10, may exhibit a higher turn-on resistance (and hence a slower turn on time) than would, e.g., a relatively "short" N-FET, having a size of 4/4.

TABLE 1

| Transistor or Component Ref. | Type | Dimensions/Size |
| --- | --- | --- |
| M1 | NFET | 2.4/10 |
| M2 | NFET | 4/1.2 |
| M3 | NFET | 2.4/10 |
| M4 | NFET | 4/1.2 |
| M5 | NFET | 2.4/10 |
| M6 | NFET | 4/1.2 |
| M7 | NFET | 4/1.2 |
| M8 | NFET | 4/1.2 |
| M9 (not used) | — | — |
| M10 | PFET | 3/24 |
| M11 | PFET | 5/10 |
| M12 | PFET | 5/10 |
| M13 | NFET | 5/10 |
| M14 | NFET | 5/10 |
| M15 | PFET | 2.4/2 |
| M16 | NFET | 4/4 |
| M17 | NFET | 4/1.2 |
| M18 | PFET | 2.4/2 |
| M19 | NFET | 4/4 |
| M20 | NFET | 4/1.2 |
| M21 | PFET | 2.4/4 |
| M22 | NFET | 4/4 |
| M23 | PFET | 4/1.2 |
| M24 | PFET | 2.4/1.2 |
| M25 | PFET | 2.4/4 |
| M26 | NFET | 4/4 |
| M27 | PFET | 4/1.2 |
| M28 | PFET | 2.4/1.2 |
| M29 | PFET | 4/1.2 |
| M30 | NFET | 4/1.2 |
| M31 | PFET | 4/1.2 |
| M32 | NFET | 4/1.2 |
| M33 | NFET | 4/1.2 |
| M34 | NFET | 8/4 |
| M35 | NFET | 4/4 |
| R1 | RESISTOR | 200K |
| C1 | CAPACITOR | 5pF |
| C2 | CAPACITOR | 5pF |
| C3 | CAPACITOR | 40pF |
| C4 | CAPACITOR | 50pF |

Figure 10A:
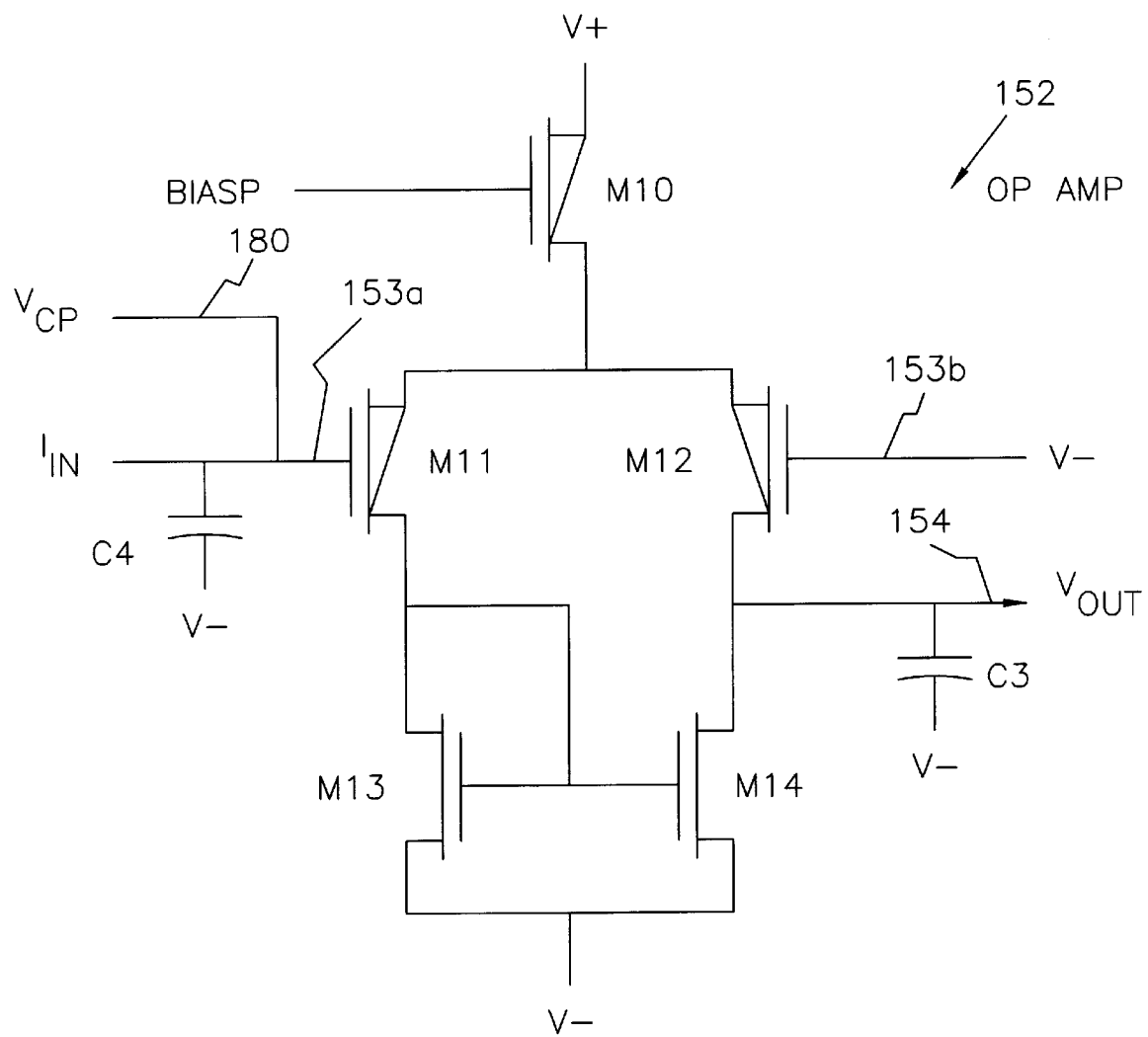
FIG. 10A shows a schematic diagram of the OP AMP portion of the I-to-F converter circuit shown in FIG. 9.
Figure 10B:
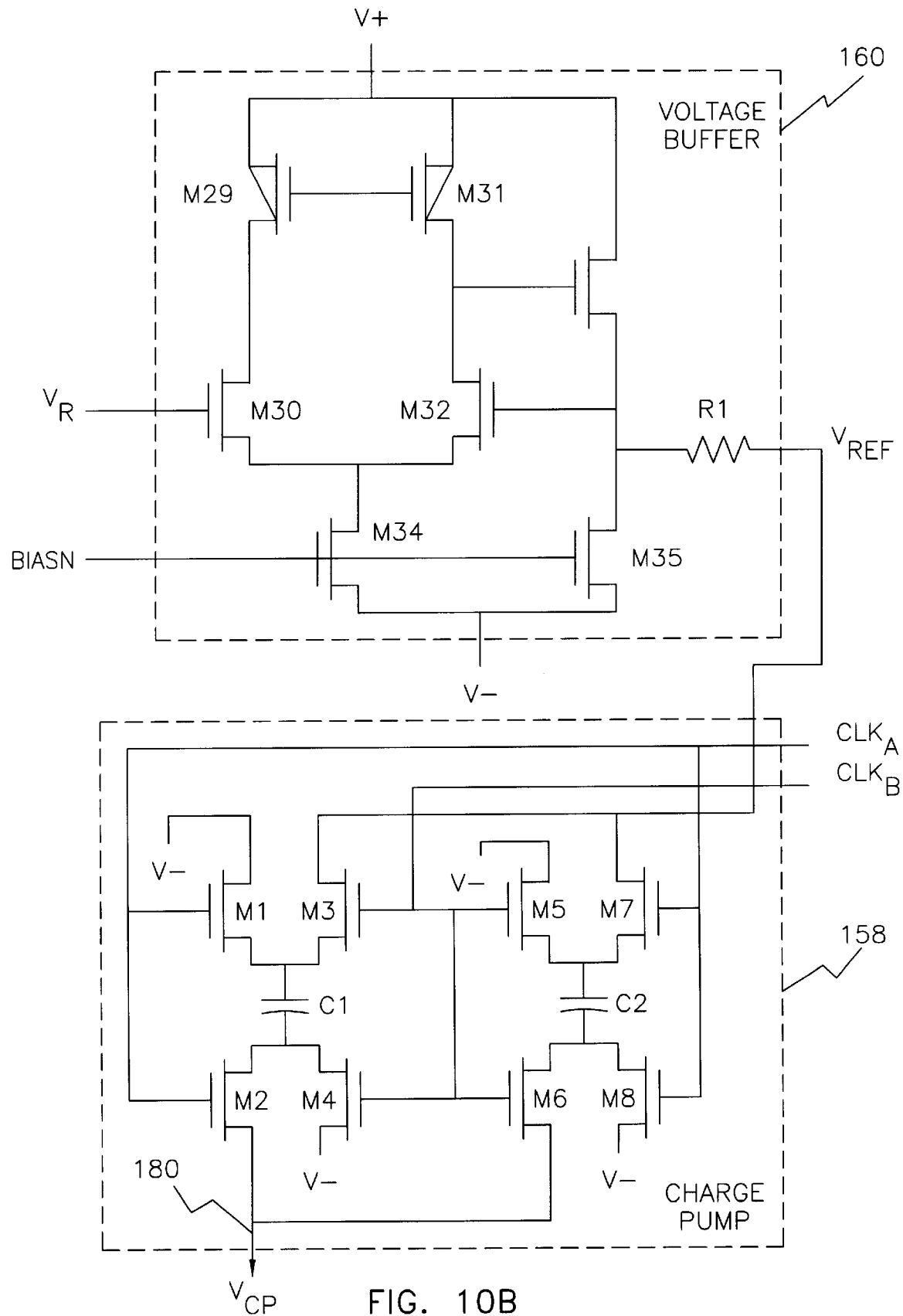
FIG. 10B shows a schematic diagram of the VOLTAGE BUFFER and CHARGE PUMP portions of the I-to-F converter circuit shown in FIG. 9.
Figure 10C:
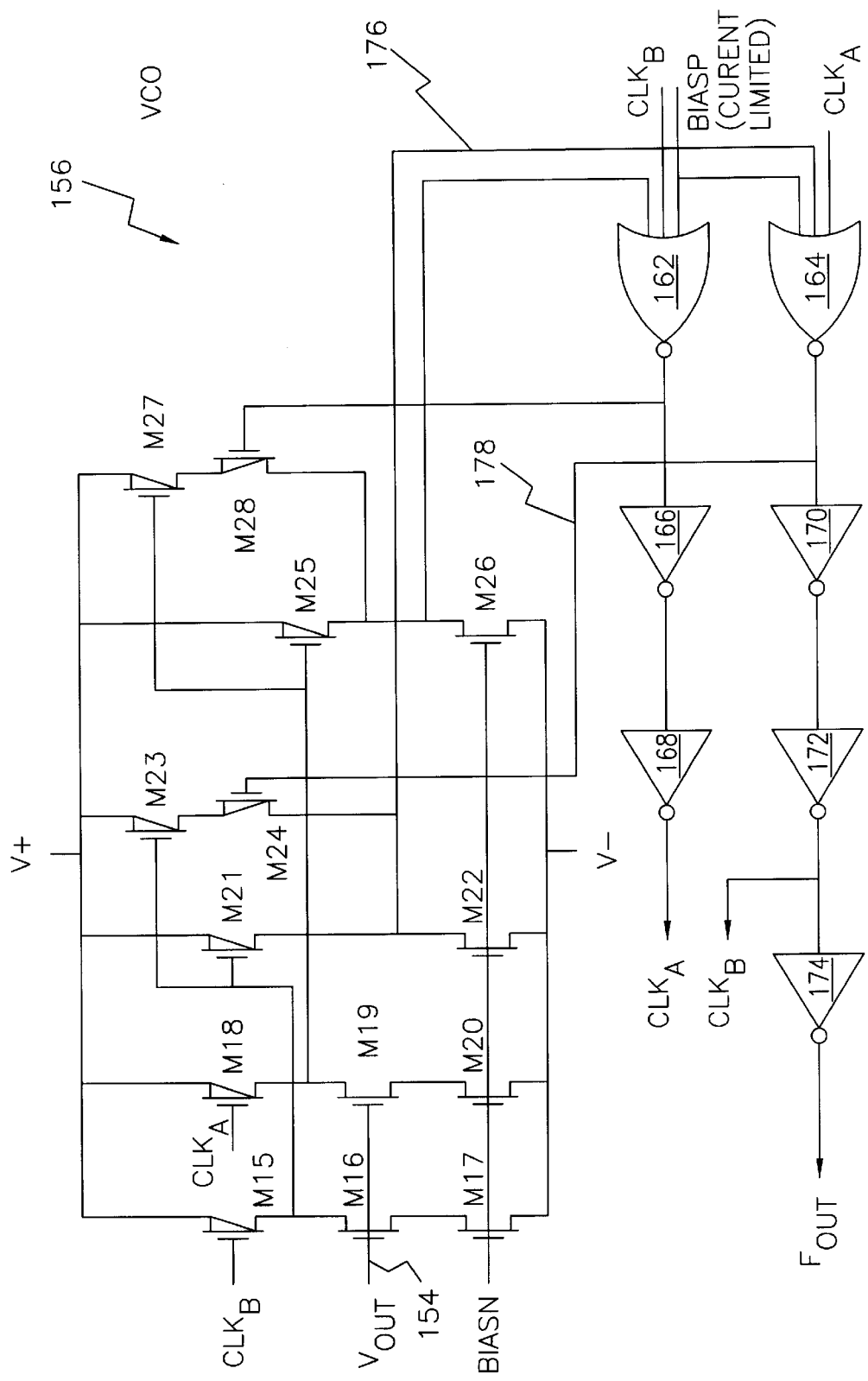
FIG. 10C shows a schematic/logic diagram of the VCO portion of the I-to-F converter circuit shown in FIG. 9.

In general, as is known in the art, a FET transistor has three terminals, a "source", a "drain" and a "gate". The voltage applied to the gate terminal controls the conductivity of the semiconductor channel that connects the source and drain terminals. By controlling the conductivity of the source-drain channel, the amount of current that flows through the channel can be controlled, from zero current to a maximum current (determined by the ON resistance and the available voltage drop across the channel). A common use for a FET transistor is as a switch. When used as a switch, the resistance of the source-drain channel, as controlled by the voltage applied to the gate terminal, is either very low (the FET switch is ON) or very high (the FET switch is OFF). For the types of FETs used in the circuits of FIGS. 10A, 10B and 10C, a high voltage applied to the gate of a P-FET tends to turn the P-FET "OFF"; whereas a high voltage applied to the gate of an N-FET tends to turn the N-FET "ON". In FIGS. 10A, 10B, and 10C, an N-FET is depicted in classical FET form, i.e., appearing generally as a forward or backwards block letter "C", made up of three segments, with one end of one segment of the "C" comprising the "source", and with one end of another segment of the "C" (which end is marked with a heavy dot nearby) comprising the "drain". The "gate" is depicted as a short line that is parallel to, but not touching, the middle segment of the "C". A P-FET is depicted the same as an N-FET except that a diagonal line is drawn through the "C".

A preferred operational amplifier (OP AMP) 152 is shown schematically in FIG. 10A. P-FET M10 is biased by an external voltage reference signal BIASP so as to form a constant current source of a few nanoamps to a differential pair of transistors M11 and M12. So long as the gate voltage applied to each of the differential pair M11 and M12 is equal, the current from the current source M10 is equally split between M11 and M12. N-FETs M13 and M14 provide a current mirror, which functions as a load for the differential pair M11 and M12. In the operation of a current mirror, an M13 pull-up current is mirrored by an M14 pull-down current, and vice-versa. Thus, the output (the drain of M12 and M14) pulls up or down depending upon the input. The gate terminal of M11 is connected to one side of a storage capacitor C4. The other side of the capacitor C4 is grounded (connected to V−). The gate terminal of M12 is connected to ground (V−). The input terminal of the OP AMP 152 comprises the gate of M11. Hence, any input current, $I_{IN}$, that flows into the OP AMP, begins to charge up C4, causing a voltage to appear at the gate of M11 that is different than the voltage applied to the gate of M12. Because transistor M11 is a P-FET transistor, a higher gate voltage (as would occur when an input current $I_{IN}$ starts to charge capacitor C4) tends to turn M11 OFF (increases its resistance). This increase in resistance, in turn, causes the constant current from the current source M10 to be unevenly split between the two M11/M12 paths. More particularly, an increase in the input voltage applied to the gate of M11 (caused by applying an input current $I_{IN}$ so as to charge up the capacitor C4) causes an increased current to flow through the M12 leg of the OP AMP, thereby causing the output voltage, $V_{OUT}$ (which is the voltage at the drain of M12), on signal line 154, as measured relative to ground (V−), to increase. By properly selecting the transistor dimensions and operating conditions, the "gain" of the OP AMP (where "gain" is defined, for purposes of the OP AMP shown in FIG. 10A, as the ratio of $V_{OUT}/V_{IN}$, where $V_{IN}$ is the voltage developed on the capacitor C4 by the current $I_{IN}$) can thus be made sufficiently large, on the order of 100, to support the desired overall operation of the I-to-F circuit.

With the inputs of the M11/M12 differential pair being maintained at or near zero, and with the combination of the threshold BIASP plus the voltage applied to the body (or substrate) of the P-FETS (which is typically V+, or about 3 volts), the output voltage $V_{OUT}$ Of the OP AMP 152 may swing from near ground (V−) to about 1.5 volts. A capacitor C3 is connected between the output terminal of the OP AMP (drain of M12) and filters this output voltage to a desired extent.

Figure 10D:
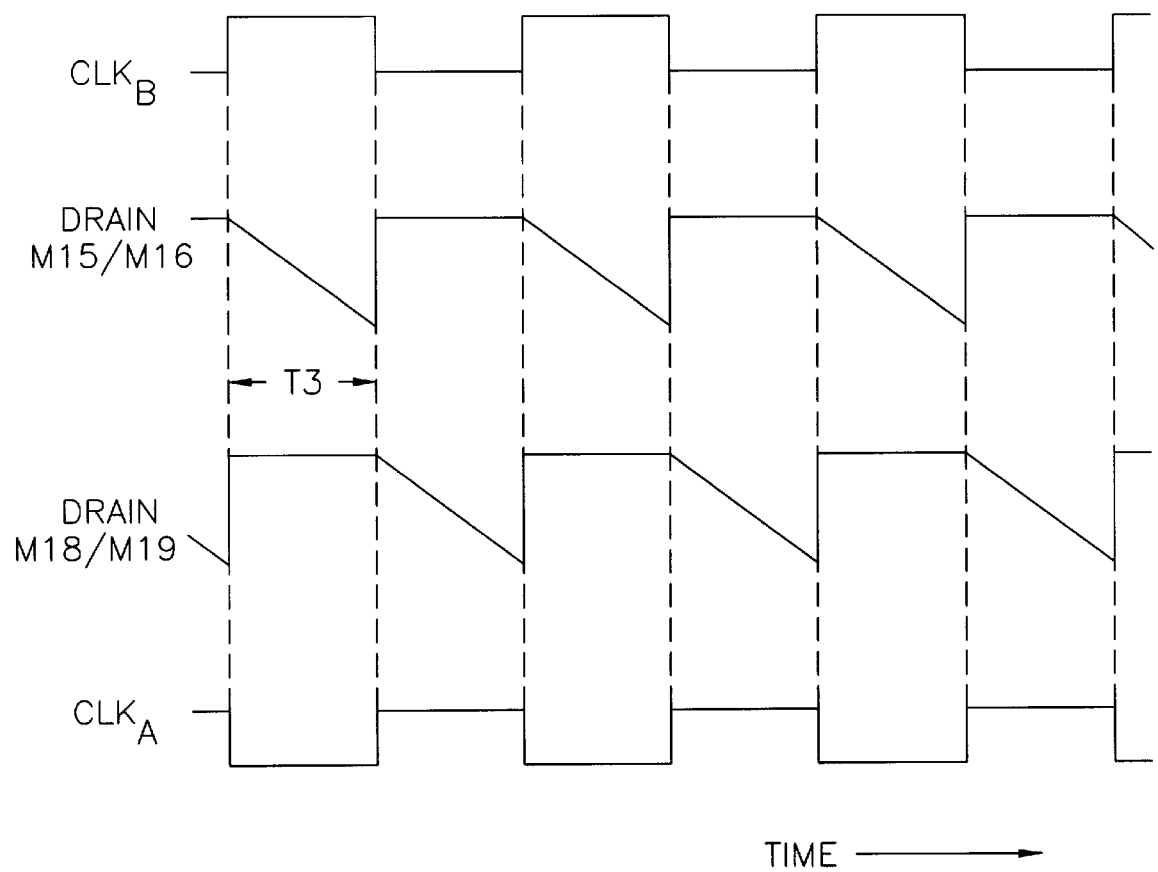
FIG. 10D shows a timing waveform diagram associated with the operation of the VCO circuit of FIG. 10C.

The output voltage $V_{OUT}$ from the OP AMP 152 (FIG. 10A), on signal line 154, is applied to the control voltage input of the VCO 156. A schematic/logic diagram of a preferred low power VCO is illustrated in FIG. 10C, and a timing waveform diagram that illustrates the basic operation of the VCO 156 is shown in FIG. 10D. For simplicity, gates 162 through 174 included in the low power VCO of FIG. 10C (which are configured as a cross-coupled latch with active-high inputs) are shown in logic diagram form It is to be understood, however, that such gates are preferably configured using additional N-FET and P-FET transistors, as is known in the art.

The operation of the VCO is best understood by considering what happens just after the output of gate 172 (identified in FIG. 10C and 10D as $CLK_B$) goes high. This turns off M15 and allows the drain of M15 (which is the same point as the drain of M16) to ramp toward ground (V−), as seen in FIG. 10D. The slope of the ramp depends on the capacitance on the drain node and on the drain current (and hence gate voltage) of M16. When the drain voltage of M15/M16 ramps down to about one threshold below V+, P-FET M21 turns ON, causing an input of gate 164 to go positive over signal line 176 (FIG. 10C). As the logic threshold of gate 164 is reached, the output of gate 164 goes low, turning on M24 (via signal line 178). This action provides hysteresis by reinforcing the high-going signal at the input of gate 164 (via signal line 176). A short time later, the output of gate 164 reaches the logic threshold of gate 170, and the latch (i.e., the cross-coupled latch with active-high inputs made up of gates 162–172) flips state.

Once the state of the cross-coupled latch has switched, the output of gate 172 goes low, and the output of gate 168 ($CLK_A$) goes high, and the sequence repeats, but with M18, M25, and gate 162 in the signal path. During this repeat time, the drain of M15/16 remains high, while the drain of M18 (which is the same point as the drain of M19) ramps toward ground (V−) at a rate that depends on the capacitance on the drain node and on the drain current of (and hence the drain voltage) of M19. As seen in FIG. 10D, this results in the generation of two complimentary clock signals, $CLK_A$ and $CLK_B$, with an output signal $F_{OUT}$ being derived from the $CLK_B$ signal, as buffered by inverter gate 174.

During the operation described above, N-FETs M17 and M20 function as current sources that limit the capacitance charging current in the VCO to about 50 na. Such limiting prevents a lockup conduction which would otherwise occur if the VCO attempted to operate above its normal maximum frequency. In operation, the nominal frequency of the VCO 156 is about 10 KHz, with a typical minimum operating frequency of 1 KHz, and a typical maximum operating frequency of 30 KHz.

It is noted that the frequency versus voltage relationship of the VCO shown in FIG. 10C is not linear (since it depends on the drain current versus gate voltages of N-FETs M16 and M19). However, as evident from the description of the operation of the complete I-to-F converter, the overall current-to-frequency linearity depends only on the repeatability of the charge pump, and that is designed, as explained below, to pump a fixed charge that is less than 10 picocoulombs, e.g., about 6 picocoulombs (pC), with every flip of the VCO.

One special feature associated with the VCO 156 shown in FIG. 10C is that the NOR gates 162 and 164 each include a series bias FET that limits the supply current to less than 100 na when the logic inputs are at voltages between the supply rails, i.e., between V+ and V−.

It is the CLK$_A$ and CLK$_B$ signals that drive the charge pump circuit 158, shown in the bottom half of FIG. 10B. The charge pump circuit 158 includes eight N-FET transistors, M1 through M8. In operation, the charge pump circuit emits fixed size packets of charge to the circuit input node, over signal line 180. The amount of charge is determined by the value of capacitors C1 and C2 and by a reference voltage V$_{REF}$. The reference voltage V$_{REF}$ comprises a buffered reference voltage that is generated by the voltage buffer circuit 160, shown in the upper half of FIG. 10B. Other reference voltages used by the I-to-F converter circuit 150 include an unbuffered reference voltage V$_R$, a BIASP reference voltage, and a BIASN reference voltage.

The operation of the charge pump circuit 158 is as follows: during one state of the VCO, i.e., when CLK$_A$ is low and CLK$_B$ is high, M3 and M4 are ON, and M1 and M2 are OFF. In this condition, capacitor C1 charges to the reference voltage, V$_{REF}$. When the VCO state flips, i.e., when CLK$_A$ goes high and CLK$_B$ goes low, M3 and M4 turn OFF, and then M1 and M2 turn ON. This then causes C1 to discharge via signal line 180 (which is connected to the input of the OP AMP 152), causing the otherwise high-going input signal line (recall that input current I$_{IN}$ is charging capacitor C4) to be pulled back towards ground (V−).

The second capacitor C2 works in tandem with the first capacitor C1. That is, while capacitor C1 is charging up to V$_{REF}$, capacitor C2 is discharging via signal line 180 back to ground (V−). While capacitor C2 is charging up to V$_{REF}$, capacitor C1 is discharging via signal line 180 back to ground. Each time that C1 or C2 discharges, it pulls charge off of the input capacitor C4 via signal line 180. The net result is that the I-to-F converter maintains the input terminal 153$a$ of the OP AMP 152 at the same potential as the input 153$b$, which is V− (ground).

Thus, it is seen that with each flip of the VCO, a charge packet is pumped off of the input capacitor C4. Since these charge packets are the only current flowing from the sensor, and since they are all the same size, their frequency is directly related to the input current I$_{IN}$.

The sizes of the various FETs used within the charge pump circuit 158, and the VCO 156, are chosen so that the capacitors C1 and C2 are fully charged and discharged during each phase of the VCO operation, even at the highest frequencies of normal operation The timing of the two VCO outputs, CLK$_A$ and CLK$_B$, ensures a break-before-make action on the switches connected to the charge pump capacitors C1 and C2.

In summary, all of the sensor current I$_{IN}$ that is collected by capacitor C4 is pumped off of the capacitor C4 by the charge pump circuit. As soon as the input current I$_{IN}$ tries to pull the circuit input 153$a$ away from ground, the OP AMP output causes the VCO to speed up, which in turn causes more negative-going charge packets to be emitted by the charge pump 158, which pulls the circuit input 153$a$ back to ground.

In order to prevent cross talk due to transient loading of V$_{REF}$, the voltage buffer circuit 160 is employed. Such buffer circuit comprises, as seen in the upper half of FIG. 10B, a conventional OP AMP follower circuit composed of FET transistors M29–M35.

The overall power consumption of the I-to-F converter circuit described in connection with FIG. 10 is only about 1.8 microwatts (assuming a 3 volt operating voltage, and 600 na operating current) The quiescent operating current of the device is less than about 100 na. Such low power operation is one of the salient features of the I-to-F converter circuit of the present invention.

Another important feature of the invention is that the input terminal of the I-to-F converter circuit 150, which is terminal 153$a$ of the OP AMP 152, is maintained at essentially ground potential without the necessity of a second voltage supply. That is, in a conventional OP AMP, in order to maintain the inputs at zero volts, one would have to bias the OP AMP with a voltage greater than zero, e.g., +5 volts, and a voltage less than zero, e.g., −5 volts, thereby forcing the use of two separate voltage supplies. However, by using the charge pump, as shown in FIG. 10A, it is possible to maintain the inputs at or near zero, even though the OP AMP itself is only biased with a single supply between V+ and V− (ground).

As described above, it is thus seen that the present invention provides a low power current-to-frequency converter circuit usable, e.g., in an implantable sensor device wherein there is a need to convert a low level analog signal, such as a very small electrical dc current, the magnitude of which is representative of a sensed parameter or substance, to a digital value that can be better transmitted over a shared communication bus to a remote receiver.

While the invention herein disclosed has been described by means of specific embodiments and applications thereof, numerous modifications and variations could be made thereto by those skilled in the art without departing from the scope of the invention set forth in the claims.

What is claimed is:

1. A low power current-to-frequency (I-to-F) converter circuit for use within an implantable device, comprising:

an amplifier having two input terminals and an output terminal, the amplifier comprising means for differentially amplifying an electrical signal applied between its two input terminals to provide an amplified output signal V$_{OUT}$ appearing on its output terminal;

a first capacitor electrically connected to at least one of the input terminals of the amplifier;

a voltage controlled oscillator (VCO) circuit having a voltage-control input terminal and a VCO output terminal, the voltage-control input terminal being connected to the output terminal of the amplifier, the VCO including means for generating a frequency output signal F$_{OUT}$ having a frequency that varies as a function of the magnitude of a voltage applied to the voltage-control input; and a charge-pump circuit coupled to the first capacitor that pumps a discrete charge off of said first capacitor under control of the frequency output signal F$_{OUT}$ generated by the VCO.

2. The low power I-tp-F converter circuit of claim 1 wherein the amplifier, VCO, and charge pump circuit are implemented on a single integrated circuit chip.

3. The low power I-to-F converter circuit of claim 1 wherein the amplifier, VCO and charge pump circuit all operate using one supply voltage having a first terminal V+, and a second terminal V−, and wherein the first of the two capacitors is connected between a first input terminals of the amplifier and V−, and a second of the two input terminals of the amplifier is also connected to V−.

4. The low power I-to-F converter circuit of claim 3 wherein the I-to-F converter circuit is made up of semiconductor circuit components that consume less than 600 nanoamps (na) of current.

5. The low power I-to-F converter circuit of claim 1 further including logic circuits responsive to the V$_{OUT}$ signal to control the charge pump circuit to pump the discrete charge off of the first capacitor at least once during each cycle of the F$_{OUT}$ signal.

6. The low power I-tp-F converter circuit of claim 5 wherein the amplifier, VCO, logic circuits, and charge pump circuit are implemented on a single integrated circuit chip.

7. The low power I-to-F converter circuit of claim 5 wherein the discrete charge pumped off of the first capacitor at least once during each cycle of the $F_{OUT}$ signal comprises a charge no greater than about 10 picocoulombs.

8. The low power I-to-F converter circuit of claim 7 wherein the logic circuits generate a clock signal having a first phase and a second phase, and wherein the charge pump circuit comprises means for receiving a reference voltage $V_{REF}$, a second capacitor, a first set of switches for charging the second capacitor to the reference voltage $V_{REF}$ during the first phase of the clock signal, and a second set of switches for connecting the second capacitor across the first capacitor with opposing polarity during the second phase of the clock signal, whereby the $V_{REF}$ charge that accumulates on the second capacitor during the first phase of the clock signal is pulled off of the first capacitor during the second phase of the clock signal.

9. The low power I-to-F converter circuit of claim 8 wherein the charge pump circuit further includes:

a third capacitor, and a plurality of switches of the second set of switches charges the third capacitor to the reference voltage $V_{REF}$ during the second phase of the clock signal, a plurality of switches of the first set of switches connect the third capacitor across the first capacitor with opposing polarity during the first phase of the clock signal, and the $V_{REF}$ charge that accumulates on the third capacitor during the second phase of the clock signal is pulled off of the first capacitor during the first phase of the clock signal.

10. An implantable sensor comprising:

a sensor that generates an analog current as a function of a substance or parameter sensed by the sensor;

a current-to-frequency (I-to-F) converter circuit that converts the analog current generated by the sensor to a frequency signal, $F_{OUT}$, having a frequency that varies as a function of the analog current, said I-to-F converter circuit comprising:

an amplifier having a positive input terminal, a negative input terminal, and an output terminal, the amplifier including means for differentially amplifying an electrical signal applied between its two input terminals to provide an amplified output signal that appears on its output terminal;

a first capacitor connected to one of the input terminals of the amplifier;

a voltage controlled oscillator (VCO) circuit having a voltage-control input terminal connected to the output terminal of the amplifier, and a VCO output terminal, the VCO including means for generating the frequency signal $F_{OUT}$ as an output signal of the VCO, the signal $F_{OUT}$ having a frequency that varies as a function of the magnitude of a voltage applied to the voltage-control input;

a charge-pump circuit coupled to the first capacitor that pumps a discrete charge off of the first capacitor under control of the frequency of the signal $F_{OUT}$;

wherein the analog current from the sensor is applied to the first capacitor and tends to cause a charge to accumulate on the first capacitor as a function of the magnitude of the analog current, which charge tends to increase the output voltage of the amplifier so as to increase the frequency of the signal $F_{OUT}$, which increased frequency causes charge to be pumped off of the first capacitor at an increased rate, wherein the amplifier forces the frequency of the $F_{OUT}$ signal to whatever rate is needed to maintain the charge on the first capacitor at essentially zero, whereby the frequency of the VCO output signal varies as a function of the magnitude of the analog current applied to the first capacitor.

11. The implantable sensor of claim 10 wherein the amplifier, VCO and charge pump circuit all operate using one supply voltage having a first terminal V+, and a second terminal V−, and wherein the first capacitor is connected between one of the positive and negative input terminals of the amplifier and V−, and the other input terminal of the amplifier is also connected to V−.

12. The implantable sensor of claim 11 further including logic circuitry responsive to the frequency signal $F_{OUT}$ generated by the VCO to control the charge pump circuit to pump the discrete charge off of the first capacitor at least once during each cycle of the $F_{OUT}$ signal.

13. The implantable sensor of claim 12 wherein the discrete charge pumped off of the first capacitor at least once during each cycle of the $F_{OUT}$ signal comprises a charge no greater than about 10 picocoulombs.

14. The implantable sensor of claim 13 wherein the amplifier, VCO, charge pump circuit and logic circuitry are realized on a single integrated circuit chip.

15. In an implantable medical device, a low power current-to-frequency converter comprising:

an amplifier having two input terminals and one output terminal, the amplifier comprising means for differentially amplifying an electrical signal applied between its two input terminals to provide an amplified output signal appearing on its output terminal;

a first capacitor connected to one of the input terminals of the amplifier;

a voltage controlled oscillator (VCO) circuit having a voltage-control input terminal and a VCO output terminal, the voltage-control input terminal being connected to the output terminal of the amplifier, the VCO including means for generating a VCO signal having a frequency that varies as a function of the magnitude of a voltage applied to the voltage-control input;

a charge-pump circuit coupled to the first input terminal of the amplifier for pumping a discrete charge off of said first capacitor under control of the frequency of said VCO signal;

wherein the electrical current is applied to the first capacitor and tends to cause a charge to accumulate on the first capacitor as a function of the magnitude of the electrical current, which charge tends to increase the output voltage of the amplifier so as to increase the frequency of the VCO signal, which increased VCO frequency causes the charge to be pumped off of the first capacitor at an increased rate, wherein the amplifier forces the frequency of the VCO signal to whatever rate is needed to maintain the charge on the first capacitor at essentially zero, whereby the frequency of the VCO signal varies as a function of the magnitude of the electrical current applied to the first capacitor.

16. The low power current-to-frequency converter of claim 15 wherein the amplifier, VCO and charge pump circuit all operate using one supply voltage having a first terminal V+, and a second terminal V−, and wherein the first capacitor is connected between a first input terminal of the operational amplifier and V−, and a second input terminal of the operational amplifier is also connected to V−.

17. The low power current-to-frequency converter of claim 16 wherein the current-to-frequency converter consumes less than about 600 nanoamps (na) of current.

18. The low power current-to-frequency converter of claim 15 further including a latch logic circuit coupled to the VCO for generating a clock signal for controlling the charge pump circuit to pump the discrete charge off of the first capacitor at least once during each cycle of the clock signal.

19. The low power current-to-frequency converter of claim 18 wherein the discrete charge pumped off of the first capacitor at least once during each cycle of the clock signal comprises a charge no greater than about 10 picocoulombs.

20. The low power current-to-frequency converter of claim 18 wherein the clock signal has a first phase and a second phase, and wherein the charge pump circuit comprises a second capacitor, a first set of switches for charging the second capacitor to a reference voltage $V_{REF}$ during the first phase of the clock signal, and a second set of switches for connecting the second capacitor across the first capacitor with opposing polarity during the second phase of the clock signal, whereby the $V_{REF}$ charge that accumulates on the second capacitor during the first phase of the clock signal is pulled off of the first capacitor during the second phase of the clock signal.

21. The low power current-to-frequency converter of claim 20 wherein the charge pump circuit further includes:

a third capacitor, and a plurality of switches of the second set of switches charges the third capacitor to the reference voltage $V_{REF}$ during the second phase of the clock signal, a plurality of switches of the first set of switches connect the third capacitor across the first capacitor with opposing polarity during the first phase of the clock signal, and the $V_{REF}$ charge that accumulates on the third capacitor during the second phase of the clock signal is pulled off of the first capacitor during the first phase of the clock signal.

22. The low power current-to-frequency converter of claim 15 wherein the amplifier, VCO and charge pump circuit are all realized on a single integrated circuit chip.

* * * * *

UNITED STATES PATENT AND TRADEMARK OFFICE
CERTIFICATE OF CORRECTION

PATENT NO. : 5,917,346
DATED : June 29, 1999
INVENTOR(S) : Gord

It is certified that error appears in the above-identified patent and that said Letters Patent is hereby corrected as shown below:

ON THE TITLE PAGE

Item 56, please add:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 4 | 9 | 4 | 2 | 4 | 0 | 1 | 07/17/90 | Gessaman, et al. | | | |
| | | 3 | 7 | 5 | 7 | 7 | 7 | 0 | 09/11/73 | Brayshaw et al. | | | |
| | | | | | | | | | | | | | |

FOREIGN PATENT OR PUBLISHED FOREIGN PATENT APPLICATION

| | | DOCUMENT NUMBER | | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|---|
| | | 0 | 6 | 7 | 0 | 4 | 4 | 9 A1 | 09/06/95 | EPC | | | | |
| | | 0 | 2 | 3 | 2 | 4 | 5 | 1 | 08/19/87 | EPC | | | | |
| | | | | | | | | | | | | | | |

Signed and Sealed this

Tenth Day of October, 2000

Attest:

Q. TODD DICKINSON

*Attesting Officer*  *Director of Patents and Trademarks*